United States Patent
Xue et al.

(10) Patent No.: US 11,781,117 B2
(45) Date of Patent: Oct. 10, 2023

(54) MACHINE LEARNING GENE MINING METHOD AND PHOSPHINOTHRICIN DEHYDROGENASE MUTANT FOR AMINO TRANSLOCATION

(71) Applicant: ZHEJIANG UNIVERSITY OF TECHNOLOGY, Hangzhou (CN)

(72) Inventors: Yaping Xue, Hangzhou (CN); Feng Cheng, Hangzhou (CN); Dongyang Wu, Hangzhou (CN); Shuping Zou, Hangzhou (CN); Jianmiao Xu, Hangzhou (CN); Yuguo Zheng, Hangzhou (CN)

(73) Assignee: ZHEJIANG UNIVERSITY OF TECHNOLOGY, Hangzhou (CN)

( * ) Notice: Subject to any disclaimer, the term of this patent is extended or adjusted under 35 U.S.C. 154(b) by 0 days.

(21) Appl. No.: 17/505,945

(22) Filed: Oct. 20, 2021

(65) Prior Publication Data

US 2022/0204948 A1    Jun. 30, 2022

(30) Foreign Application Priority Data

Dec. 31, 2020  (CN) .......................... 202011644056.2

(51) Int. Cl.
| | |
|---|---|
| *C12N 9/06* | (2006.01) |
| *C12P 13/04* | (2006.01) |
| *G16B 30/10* | (2019.01) |
| *C12N 9/04* | (2006.01) |
| *C12N 1/21* | (2006.01) |
| *C12N 15/53* | (2006.01) |

(52) U.S. Cl.
CPC ......... *C12N 9/0016* (2013.01); *C12N 9/0006* (2013.01); *C12P 13/04* (2013.01); *G16B 30/10* (2019.02); *C12Y 104/01002* (2013.01); *C12Y 104/01003* (2013.01); *C12Y 104/01004* (2013.01)

(58) Field of Classification Search
None
See application file for complete search history.

(56) References Cited

U.S. PATENT DOCUMENTS

| | | | | |
|---|---|---|---|---|
| 10,865,391 B2 * | 12/2020 | Yang | ....................... | C12P 13/04 |
| 11,339,380 B2 * | 5/2022 | Yang | ....................... | C12P 13/04 |

FOREIGN PATENT DOCUMENTS

JP    08242863 A    *   9/1996

OTHER PUBLICATIONS

Pearson, What is a gene?, Nature 441, 2006, 399-401. (Year: 2006).*
Cheng et al., Tuning amino acid dehydrogenases with featured sequences for L-phosphinothricin synthesis by reductive amination, J. Biotechnol. 312, 2020, 35-43. (Year: 2020).*
Cheng et al., Simultaneous Directed Evolution of Coupled Enzymes for Efficient Asymmetric Synthesis of L-Phosphinothricin, Appl. Environ. Microbiol 87, Mar. 2021, e02563-20. (Year: 2021).*

* cited by examiner

*Primary Examiner* — Todd M Epstein
(74) *Attorney, Agent, or Firm* — Jiwen Chen; Joywin IP Law PLLC

(57) ABSTRACT

Disclosed are a machine learning gene mining method and a phosphinothricin dehydrogenase mutant for amino translocation. The phosphinothricin dehydrogenase mutant for amino translocation is obtained by mutation of a wild-type phosphinothricin dehydrogenase with an amino acid sequence as shown in SEQ ID No.2 at one of the following sites: (1) E263D-K134R-H96A-R290V; (2) E263D-K134R-H96A; (3) E263D-K134R; (4) E263D; (5) E263N; (6) E263C; and (7) E263G. The present invention utilizes the site-saturation mutagenesis technology to mutate a phosphinothricin dehydrogenase gene as shown in SEQ ID No. 1, finds that the 263rd, 134th, 290th and 290th positions are the key sites affecting enzyme activity and stereoselectivity, and obtains a mutant with enzyme activity and ee value much higher than those of the parent phosphinothricin dehydrogenase.

8 Claims, 4 Drawing Sheets

Specification includes a Sequence Listing.

MACHINE LEARNING GENE MINING METHOD AND PHOSPHINOTHRICIN DEHYDROGENASE MUTANT FOR AMINO TRANSLOCATION

Applicant hereby electronically submits the Sequence Listing in ASCII text file (CRF format) with the file name of P76185USO_SEQ_LIST_ST25.txt, created on Oct. 20, 2021 and with the size of 12,288 bytes, which is hereby incorporated by reference. It is respectfully submitted that the Sequence Listing in CRF format does not include new matter. In addition, the Sequence Listings hereby submitted satisfy both the paper copy requirement under 37 CFR 1.821(c) and the computer-readable form requirement of 37 CFR 1.182(e). Thus, the requirement of 37 CFR 1.821(f) has been satisfied.

FIELD OF TECHNOLOGY

The present invention relates to the field of biotechnology, in particular to a machine learning-aided gene mining method and a phosphinothricin dehydrogenase mutant for amino translocation.

BACKGROUND TECHNOLOGY

Phosphinothricin (also known as glufosinate, PPT for short), with a chemical name of 2-amino-4-[hydroxy (methyl)phosphono]-butyric acid, is the second largest herbicide tolerated by transgenic crops in the world. It was first developed and produced by Hoechst (which is now owned by Bayer after several mergers). Phosphinothricin is also known as glufosinate ammonium salt, Basta and Buster. Phosphinothricin belongs to phosphonic acid herbicides and non-selective (killing) contact herbicides and is a glutamine synthetase inhibitor.

Phosphinothricin has two optical isomers, L-phosphinothricin and D-phosphinothricin. However, only the L-form has physiological activity, and is easily decomposed in the soil, is less toxic to humans and animals, has a broad herbicidal spectrum and is less destructive to the environment.

Phosphinothricin currently available on the market is generally a racemic mixture. If the phosphinothricin product can be used as a pure optical isomer in the L-configuration, the consumption of phosphinothricin can be remarkably reduced, which is of great significance for improving atomic economy, reducing use cost and lowering environmental pressure.

There are three main methods for preparing chiral pure L-phosphinothricin: chiral resolution, chemical synthesis and biocatalysis. The biocatalysis method for producing phosphinothricin has the advantages of strict stereoselectivity, mild reaction conditions, and high yield, and is an advantageous method for producing L-phosphinothricin, which mainly includes the following three categories:

1) L-phosphinothricin is obtained by direct hydrolysis of L-phosphinothricin derivatives as the substrate through an enzyme method. For this route, the main advantages are that the conversion is high, and the e.e. value of the product is high, but expensive and difficult-to-obtain chiral raw materials are needed as precursors, resulting in increased cost, which is not conductive to industrialized production. For example, the simplest process for preparing L-phosphinothricin by the biological method is to directly hydrolyze bialaphos by using protease. Bialaphos is a natural tripeptide compound, which, under the catalysis of protease, can lose two molecules of L-alanine to obtain L-phosphinothricin.

2) L-phosphinothricin is obtained through selective resolution of a precursor of racemic phosphinothricin by an enzyme. The main advantages are that the raw materials are relatively easily available, and the catalyst activity is high, but the theoretical yield can only reach 50%, resulting in the waste of raw materials. For example, Cao et al. (Cao C-H, Cheng F, Xue Y-P, Zheng Y-G (2020) Efficient synthesis of L-phosphinothricin using a novel aminoacylase mined from *Stenotrophomonas maltophilia*. Enzyme and Microbial Technology 135 doi:10.1016/j.enzmictec.2019.109493) performed chiral resolution of N-acetyl-PPT using a novel aminoacylase derived from *Stenotrophomonas maltophilia* to obtain L-phosphinothricin. Whole cells were used for catalysis, the conversion was >49% in 4 hours and optically pure L-PPT (>99.9% e.e.) was obtained.

3) With α-keto acid-2-carbonyl-4-(hydroxymethylphosphono)butyric acid (PPO) as the substrate, L-phosphinothricin is obtained by asymmetric synthesis with enzymes, mainly including transaminase and phosphinothricin dehydrogenase. Bartsch et al. (Bartsch K (2005) Process for the preparation of 1-phosphinothrcine by enzymatic transamination with aspartate. U.S. Pat. No. 6,936,444B1) used PPO as the substrate, L-aspartic acid as the amino donor to react as catalyzed by transaminase screened and separated from soil microorganisms and having specific enzymatic activity for PPO and L-aspartic acid. With a substrate concentration of 552 mM, the reaction was carried out at a very high temperature (80° C.) for 4 hours, and the conversion reached 52%, and the space-time yield was 4.5 g L-PPT/g of biocatalyst/h. However, preparation of L-phosphinothricin using transaminase has two major defects. One is that this is a reversible reaction, the raw material PPO cannot be completely converted into L-PPT, and it is impossible for the conversion to reach 100%; second, to make the reversible reaction proceed in the direction of producing L-PPT, at least 2 times of L-aspartic acid as the amino donor is needed, whereas excessive aspartic acid brings great trouble to the separation of L-PPT.

Among various enzymatic synthesis routes of phosphinothricin, the ketocarbonyl group in the keto acid intermediate is a latent chiral functional group, with which a chiral center can be constructed through an enzymatic synthesis route; and the keto acid route becomes a route suitable for industrial development and production of L-phosphinothricin because the raw materials are cheap and readily available, and the use of highly toxic cyanides can be avoided.

Amino acid dehydrogenase (EC 1.4.1.X, AADH) is a kind of amino acid dehydrogenase that can achieve reversible deamination of amino acids to produce the corresponding keto acids, which requires the participation of nucleoside coenzyme (NAD(P)$^+$) in the reaction. It has been widely used in the synthesis of natural and non-natural α-amino acids. According to their substrate specificity, amino acid dehydrogenases can be divided into glutamate dehydrogenase, leucine dehydrogenase, alanine dehydrogenase, and valine dehydrogenase or the like. An amino acid dehydrogenase will be called "phosphinothricin dehydrogenase (PPTDH)" if it shows activity towards phosphinothricin precursors.

Glucose dehydrogenase (EC1.1.1.47, GDH) is an important biocatalytic coenzyme for the regeneration cycle of coenzyme NAD(P)H in the redox catalytic reaction.

At present, the industrial synthesis of L-PPT involves asymmetric synthesis and racemic resolution by chemical synthesis or biological enzyme methods. However, asymmetric synthesis methods often require expensive chiral reagents, cofactor NADP+, keto acid substrates, or harsh reaction processes that do not meet the criteria of "green chemistry". Besides, the content of NAD in cells is 100 times that of NADP, and NAD is more stable and lower in cost than NADP. Therefore, by modifying the coenzyme preference of phosphinothricin dehydrogenase, NAD and NADP can be simultaneously used as coenzyme, which is more beneficial to industrial production.

SUMMARY OF THE INVENTION

The present invention provides a phosphinothricin dehydrogenase mutant for amino translocation, an recombinant bacterium comprising a high expressed glucose dehydrogenase gene, and an application thereof in preparing L-phosphinothricin, wherein the phosphinothricin dehydrogenase in the genetically recombinant bacterium is subjected to site-directed mutagenesis, so that the phosphinothricin dehydrogenase can utilize NADH and NADPH simultaneously in synthesis of L-PPT; and in catalytic preparation of L-phosphinothricin, high substrate conversion, high space-time yield and high total turnover number can be achieved.

The present invention firstly provides a phosphinothricin dehydrogenase mutant for amino translocation, which is obtained by mutating phosphinothricin dehydrogenase derived from Pseudomonas hunanensis at one of the following sites, with the amino acid sequence of a wild-type phosphinothricin dehydrogenase as shown in SEQ ID No.2: (1) E263D-K134R-H96A-R290V; (2) E263D-K134R-H96A; (3) E263D-K134R; (4) E263D; (5) E263N; (6) E263C; and (7) E263G.

The present invention also provides a gene encoding the phosphinothricin dehydrogenase mutant for amino translocation.

The present invention also provides a genetically recombinant bacterium comprising a host cell and a target gene transformed into the host cell, wherein the target gene comprises the gene. Preferably, the target gene in the genetically recombinant bacterium further comprises a gene encoding a glucose dehydrogenase. By simultaneously cloning the gene of the phosphinothricin dehydrogenase mutant for amino translocation and the gene encoding the glucose dehydrogenase into the same host cell, the obtained genetically recombinant bacterium can simultaneously express the two enzymes. More preferably, the GenBank accession number of the gene sequence encoding the glucose dehydrogenase is KM817194.1.

The present invention also provides an application of the phosphinothricin dehydrogenase mutant for amino translocation, the gene or the genetically recombinant bacterium in preparing L-phosphinothricin.

The present invention also provides a method for preparing L-phosphinothricin, wherein 2-carbonyl-4-(hydroxymethylphosphono)butyric acid as a substrate reacts as catalyzed by a catalyst in the presence of an inorganic amino donor, a coenzyme circulation system and a corresponding co-substrate to obtain L-phosphinothricin;

The catalyst is one of:
(1) the phosphinothricin dehydrogenase mutant for amino translocation; and
(2) a genetically recombinant bacterium capable of producing the phosphinothricin dehydrogenase mutant for amino translocation or a crude enzyme liquid obtained by lysis of the genetically recombinant bacterium.

Preferably, the coenzyme circulation system is at least one of:
(1) a formate dehydrogenase coenzyme circulation system comprising a formate dehydrogenase, a formate and a coenzyme;
(2) a glucose dehydrogenase coenzyme circulation system comprising a glucose dehydrogenase, glucose and a coenzyme; and
(3) an alcohol dehydrogenase coenzyme circulation system comprising an alcohol dehydrogenase, isopropanol and a coenzyme.

More preferably, the formate dehydrogenase is derived from Lactobacillus buchneri, and the NCBI accession number of amino acid sequence thereof is WP_013726924.1; the glucose dehydrogenase is derived from Exiguobacterium sibiricum, and the NCBI accession number of encoding gene thereof is KM817194.1; the alcohol dehydrogenase is derived from Lactobacillus brevis, and the NCBI accession number of encoding gene thereof is LK055285.1.

The present invention also provides a machine learning gene mining method, which comprises the following steps:
(1) establishment of decision tree: randomly selecting sequences from a gene bank, and with regard to the configuration of a machine learning kit scikit-learn, adopting random forest, with "n_estimator" parameter set as 1000 and other parameters as default values: randomly selecting 10 samples with replacement, and training one decision tree by using the selected 10 samples as the samples at a root node of the decision tree;
(2) setting features, including:
(a) protein size: candidate proteins are 300-500 amino acids in length,
(b) necessary characteristic sequences at both ends of phosphinothricin dehydrogenase: a first segment is GGGKGG, and a second segment is one of VVTG, FVTG, VLTG, VFTG, FITG, FFTG, VVFG, FVFTG, VLFG, VFFG, FLFG, and FFFG;
(3) decision tree splitting: when each sample has the features of the step (2), when a node of the decision tree needs to be split, one feature is randomly selected from the features, and each node in the decision tree forming process is split according to the step (2) until it can no longer be split;
(4) establishing decision trees according to the steps (1) to (3) to form a random forest, putting genes in the gene bank into the random forest so as to be judged and classified by each decision tree in the random forest respectively, and selecting a tree with the largest number of genes; and
(5) performing amino acid sequence alignment on genes in the tree with the largest number of genes in the step 4 against a known phosphinothricin dehydrogenase, and selecting a gene with the highest sequence similarity as a screened phosphinothricin dehydrogenase gene.

Compared with the prior art, the present invention has the following beneficial effects:
(1) The present invention utilizes the site-saturation mutagenesis technology to mutate the phosphinothricin dehydrogenase gene as shown in SEQ ID No. 1, finds that the $263^{rd}$, $134^{th}$, $290^{th}$ and $290^{th}$ positions are the key sites affecting enzyme activity and stereoselectivity, and obtains a mutant with enzyme activity and ee value much higher than those of the parent phosphinothricin dehydrogenase.
(2) The method for preparing L-phosphinothricin provided by the present invention can use PPO as a substrate to react directly, with NAD or NADP as a coenzyme, glucose as a co-substrate, and ammonium sulfate as an inorganic ammonium donor in the reaction process; and under the action of the mutant PhPPTDH-V375S-I167M-E263D, the highest conversion is 100 percent, and the method is of value in application.

DESCRIPTION OF THE EMBODIMENTS

Example 1

Machine Learning (Random Forest Strategy) Gene Mining of Phosphinothricin Dehydrogenase Gene (1) Establishment of decision tree: 100,000 sequences were randomly selected from an NCBI microbial gene bank; for these 100,000 sequences, the machine learning tool kit scikit-learn was configured using the random forest, with n_estimator parameter set as 1000, and the remaining parameters as default values: 10 samples were randomly selected with replacement (select one sample at a time at random, and then return to continue the selection), and the selected 10 samples were used to train a decision tree as the samples at a root node of the decision tree.

(2) Setting features (attributes): (a) protein size: length of candidate proteins (300-500 amino acids); (b) necessary characteristic sequences at both ends of phosphinothricin dehydrogenase (i.e., only the enzyme containing both sequences can be a phosphinothricin dehydrogenase): a first segment was GGGKGG, and a second segment was one of VVTG, FVTG, VLTG, VFTG, FITG, FFTG, VVFG, FVFTG, VLFG, VFFG, FLFG, and FFFG.

(3) Decision tree splitting: when each sample had the above three attributes, when a node of the decision tree needed to be split, one attribute was randomly selected from the three attributes. Each node in the decision tree formation process was split according to the step (2) (until it could no longer be split).

(4) 246 decision trees were established according to the steps 1 to 3 to form a random forest. Then, all genes in the NCBI microbial gene bank were put into the forest to be judged and classified by each decision tree in the forest respectively, and the tree with the largest number of genes was selected.

(5) The amino acid sequences of these genes were aligned with a known phosphinothricin dehydrogenase (WP_060477601.1). A phosphinothricin dehydrogenase (PhPPTDH, Genbank: WP_179026919.1, with an amino acid sequence as shown in SEQ ID No. 2, derived from *Pseudomonas hunanensis*) with the highest sequence similarity was selected.

Example 2

Construction of Genetically Recombinant Bacterium

Figure 1:
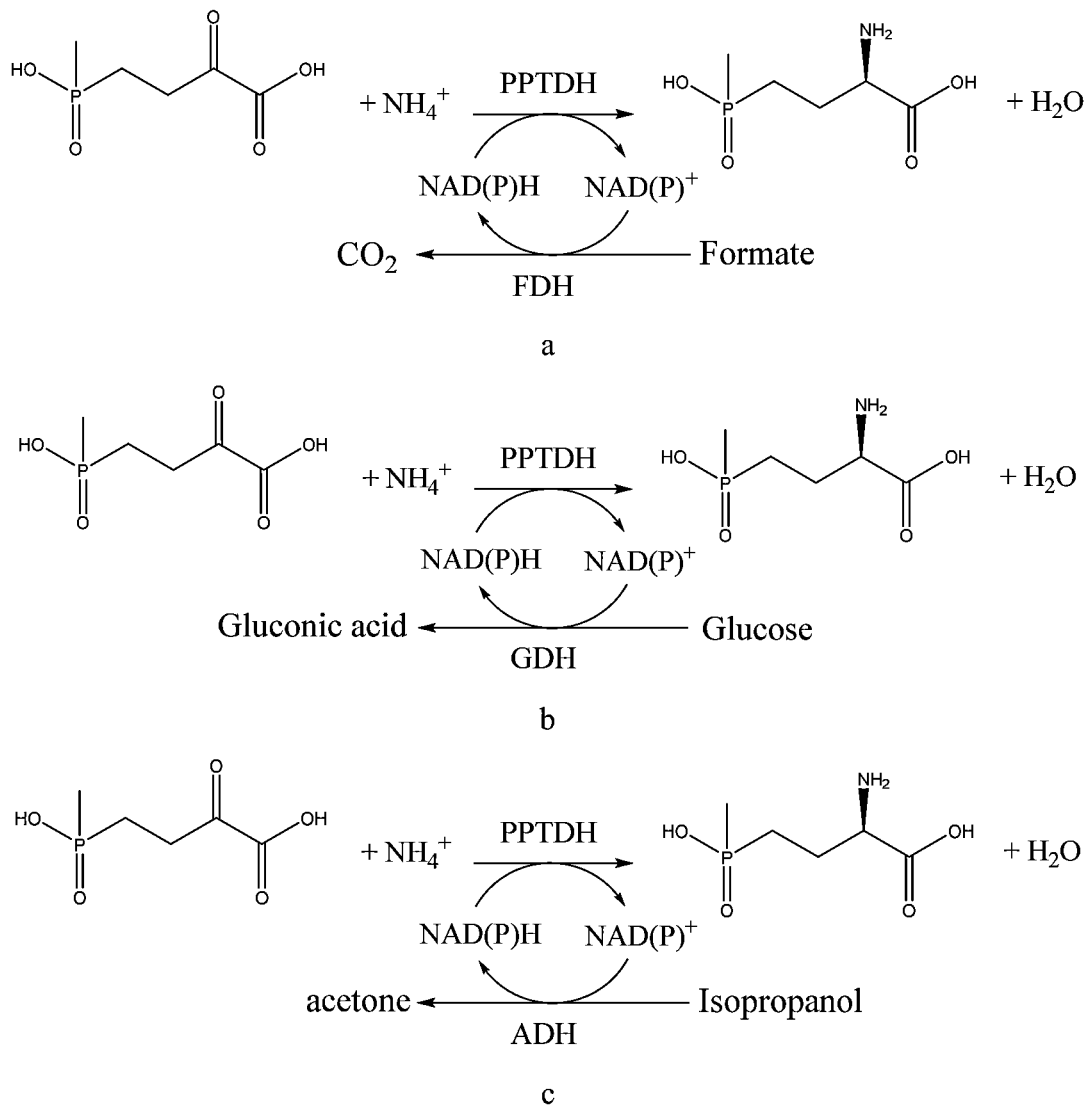
FIG. 1 is a schematic diagram showing preparation of L-PPT by asymmetric reductive amination of PPO catalyzed by PPTDH double enzyme coupling, wherein FIG. 1 (a) shows PPTDH coupled with a glucose dehydrogenase, FIG. 1 (b) shows PPTDH coupled with a formate dehydrogenase, and FIG. 1 (c) shows PPTDH coupled with an alcohol dehydrogenase.

FIG. 1 is the reaction diagram for production of L-PPT through amino translocation as catalyzed by a genetically recombinant bacterium with coupled ammonium phosphine dehydrogenase and glucose dehydrogenase double enzymes, wherein FIG. 1 (a) shows PPTDH coupled with a glucose dehydrogenase, FIG. 1 (b) shows PPTDH coupled with a formate dehydrogenase, and FIG. 1 (c) shows PPTDH coupled with an alcohol dehydrogenase.

1. Construction of Genetically Recombinant Bacterium with Phosphinothricin Dehydrogenase The phosphinothricin dehydrogenase gene (nucleotide sequence as shown in SEQ ID No.1, amino acid sequence as shown in SEQ ID No. 2) was used to construct an expression vector pETDuet-PhPPTDH to transform *E. coli*, thereby obtaining an original strain *E. coli* BL21(DE3)/pETDuet-PhPPTDH.

Figure 2:
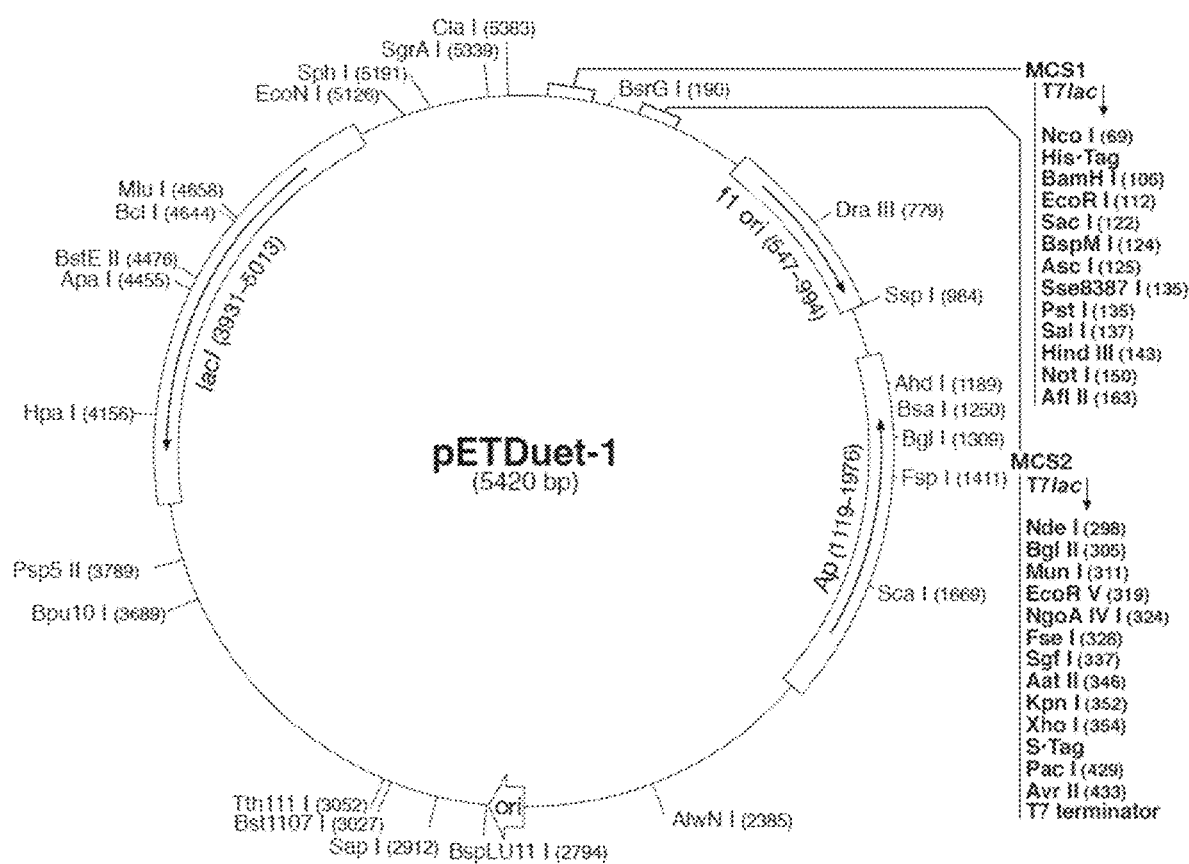
FIG. 2 is a plasmid profile of the coupled PPTDH and EsGDH expression vector obtained in Example 2.

2. Construction of Genetically Recombinant Bacterium with Coupled Phosphinothricin Dehydrogenase and Glucose Dehydrogenase A glucose dehydrogenase (GDH) gene (Genbank: KM817194.1) derived from *Exiguobacterium sibiricum* was selected to perform whole-gene synthesis to construct a genetically engineered strain *E. coli* BL21(DE3)/pETDuet-PhPPTDH-EsGDH. The plasmid profile of the obtained coupled PPTDH and EsGDH expression vector is shown in FIG. 2.

Example 3

The library of phosphinothricin dehydrogenase mutants was prepared by three rounds of site-saturation mutagenesis with primer designs shown in Table 1.

In the first round, with a vector pETDuet-PhPPTDH as a template, and the site-directed mutagenesis primers E263X-F and E263X-R in Table 1 as primers (wherein in the degenerate bases involved in the primer sequence, N represents A, C, G or T; K represents G or T; M represents A or C), PCR was conducted to mutate the glutamic acid at position 263 of the phosphinothricin dehydrogenase amino acid sequence as shown in SEQ ID No. 2 into other natural amino acids, followed by transformation, plate coating, and screening of dominant strains to obtain phosphinothricin dehydrogenase mutants PhPPTDH-E263D, PhPPTDH-E263N, PhPPTDH-E263C, and PhPPTDH-E263G, and recombinant plasmids pETDuet-PhPPTDH-E263D-EsGDH, pETDuet-PhPPTDH-E263N-EsGDH, pETDuet-PhPPTDH-E263C-EsGDH, and pETDuet-PhPPTDH-E263G-EsGDH. Among them, PhPPTDH-E263D and the recombinant plasmid pETDuet-PhPPTDH-E263D-EsGDH had the highest activity.

In the second round, with the recombinant plasmid pETDuet-PhPPTDH(E263D)-EsGDH obtained in the first round as a template and the site-directed mutagenesis primers K134X-F and K134X-R in Table 1 as primers, PCR was conducted to mutate the valine at position 134 into other natural amino acids, followed by transformation and plate coating to obtain an optimal phosphinothricin dehydrogenase mutant PhPPTDH-E263D-K134R, and the recombinant plasmid obtained by mutation was pETDuet-PhPPTDH (E263D-K134R)-EsGDH.

In the third round, with the recombinant plasmid pET-Duet-PhPPTDH(E263D-K134R)-EsGDH obtained in the second round as a template and the site-directed mutagenesis primers H96X-F and H96X-R in table 1 as primers, PCR was conducted to mutate the histidine at position 96 into other natural amino acids, followed by transformation and plate coating to obtain the optimal phosphinothricin dehydrogenase dominant mutant PhPPTDH(E263D-K134R-H96A), and the obtained recombinant plasmid was pET-Duet-PhPPTDH(E263D-K134R-H96A)-EsGDH.

In the fourth round, with the recombinant plasmid pET-Duet-PhPPTDH-E263D-K134R-H96A-EsGDH obtained in the third round as a template, and the site-directed mutagenesis primers R290X-F and R290X-R in Table 1 as primers, PCR was conducted to mutate the arginine at position 290 into other natural amino acids, followed by transformation and plate coating to obtain the optimal phosphinothricin dehydrogenase dominant mutant PhPPTDH (E263D-K134R-H96A-R290V), and the obtained recombinant plasmid was pETDuet-PhPPTDH(E263D-K134R-H96A-R290V)-EsGDH.

TABLE 1

Primer designs for phosphinothricin dehydrogenase site-directed mutagenesis

| Mutation site | Primer name | Primer sequence (5'-3') |
| --- | --- | --- |
| E263X | E263X-F | GTCTGACTCCnnkGGCACCTTGTACGCTG |
|  | E263X-R | TACAAGGTGCCmnnGGAGTCAGACAGCGA |
| K134X | K134X-F | CGACCCTnnkGGCAAGAGCGACGCTGAAG |
|  | K134X-R | GTCGCTCTTGCCmnnAGGGTCGAAGTCCG |
| H96X | H96X-F | TGCGTTTCnnkCCGTCGGTTAACCTCAGC |
|  | H96X-R | ACCGACGGmnnGAAACGCAGCCCGCCCTT |
| R290X | R290X-F | GCGCGGCnnkATCAGCGAGCTGGCCGGGC |
|  | R290X-R | TCGCTGATGCGGCCmnnCTTGACGTTCTT |

The mutation PCR system (50 μL) consisted of 25 μL of 2-fold Phanta Max buffer, 1 μL of dNTPs, 1 μL of each of upper and lower primers for mutation, 1 μL of template, 1 μL of Phanta Super-Fidelity DNA polymerase, and ddH$_2$O making up to 50 μL.

PCR conditions: pre-denaturation at 95° C. for 5 min; 30 cycles: 90° C. for 30 seconds, 58-60° C. for 30 seconds, 72° C. for 7 min; and final elongation at 72° C. for 10 min.

The PCR results were verified by DNA agarose gel electrophoresis, the PCR products were subjected to template digestion by Dpn I enzyme at 37° C. and 160 rpm for 15 min, and purified with a purification kit. E. coli BL21 (DE3) competent cells were prepared and transformed with the PCR product through heat-shock, cultured at 37° C. and 160 rpm for 1 hour, and coated on an LB plate containing 50 μg/mL ampicillin resistance to culture upside down at 37° C. overnight.

Example 4

Construction of a Gene Library of the Recombinant Enzyme (PhPPTDH)

The competent cells of E. coli BL21(DE3) (Invitrogen) stored at −80° C. were placed in an ice bath at 0° C. for 10 min, and then 5 μL of the expression vector pETDuet-1-PhPPTDH-EsGDH with the phosphinothricin dehydrogenase mutant and the glucose dehydrogenase was added thereto in a super clean bench. The mixture was placed in an ice bath at 0° C. for 30 min, heat-shocked in a water bath at 42° C. for 90 seconds, and placed in an ice bath at 0° C. for 2 min. 600 μL of LB culture medium was added thereto, and the mixture was then shaking-cultured at 37° C. and 200 rpm for 1 hour. The mixture was coated on an LB plate containing 50 μg/ml ampicillin resistance to culture at 37° C. for 8-12 hours, thereby obtaining a recombinant E. coli BL21 (DE3)/pETDuet-1-PhPPTDH-EsGDH containing the mutated phosphinothricin dehydrogenase.

Preparation of competent cells in the example: The E. coli BL21(DE3) strain preserved in a glycerol tube was obtained from a refrigerator at −80° C., streaked on an antibiotic-free LB plate to culture at 37° C. for 10 hours to obtain single colonies. The single colonies on the LB plate were picked, inoculated into a test tube containing 5 mL of LB culture medium to culture at 37° C. and 180 rpm for 9 hours. Then, 200 μL of the bacterial liquid was taken from the test tube and inoculated into 50 mL of LB culture medium to culture at 37° C. and 180 rpm until OD$_{600}$ reached 0.4-0.6. The bacterial liquid was pre-cooled on ice, put into a sterilized centrifuge tube, placed on ice for 10 min, and then centrifuged at 4° C. and 5,000 rpm for 10 min. The supernatant was poured out (contamination should be prevented), and the precipitated cells were re-suspended in pre-cooled 0.1 mol/L aqueous CaCl$_2$ solution and placed on ice for 30 min, and then centrifuged at 4° C. and 5,000 rpm for 10 min. The supernatant was discarded and the precipitated cells were re-suspended in pre-cooled 0.1 mol/L aqueous CaCl$_2$ solution containing 15% glycerol. 100 μL of the re-suspended cells were aliquoted into a sterilized 1.5 mL centrifuge tube and stored in a refrigerator at −80° C. for later use.

Example 5

Induced Expression of Parent and Mutant Phosphinothricin Dehydrogenase

Figure 3:
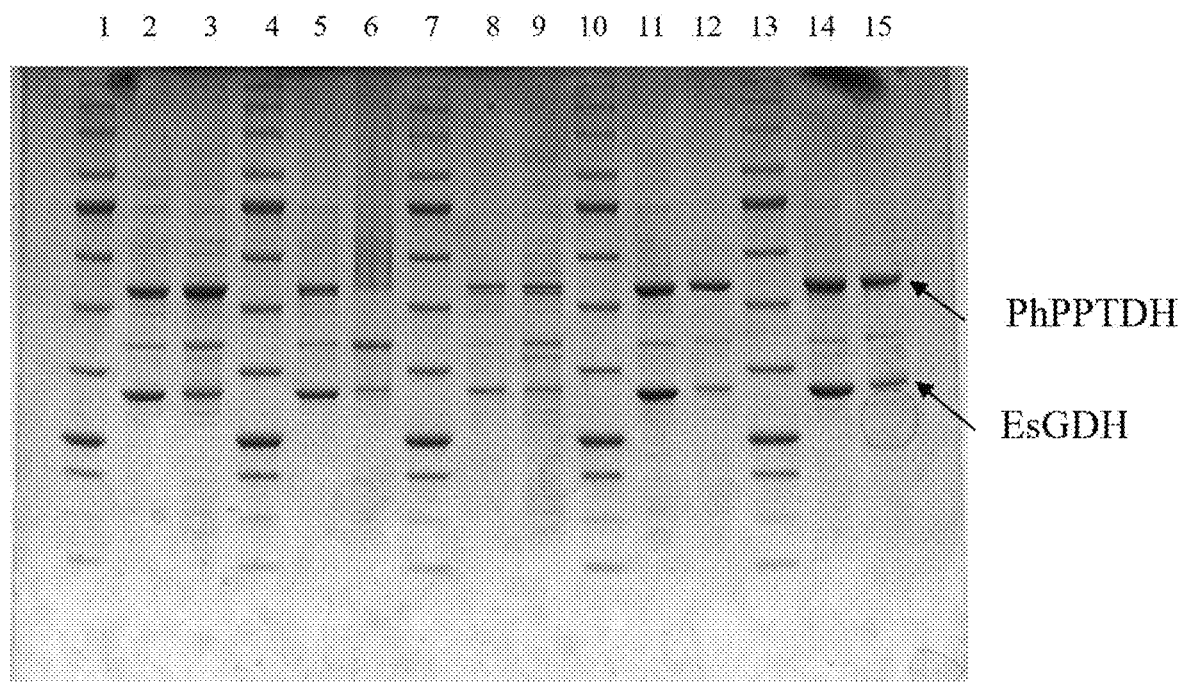
FIG. 3 is a protein gel electrophoresis image, wherein Lanes 1, 4, 7, 10 and 13 represents Marker; Lanes 2 and 3 represent the supernatant and precipitate of PhPPTDH-E263N; Lanes 5 and 6 represent the supernatant and precipitate of PhPPTDH-E263C; Lanes 8 and 9 represent the supernatant and precipitate of PhPPTDH-E263N; Lanes 11 and 12 represent the supernatant and precipitate of PhPPTDHE263G; and Lanes 14 and 15 represent the supernatant and precipitate of PhPPTDH.

The original strain pETDuet-PhPPTDH-EsGDH of the first step of Example 1 was inoculated into an LB liquid medium containing ampicillin with a final concentration of 50 μg/mL to culture at 37° C. for 8 hours, and then inoculated at a volume fraction of 2% (v/v) into a fresh LB liquid medium containing ampicillin with a final concentration of 50 μg/mL to culture at 37° C. and 180 rpm for 2 hours. Then, IPTG with a final concentration of 0.1 mM was added to the culture liquid to culture at 28° C. for 14 hours. The mixture was then centrifuged at 4° C. and 8,000 rpm for 10 min, thereby obtaining the corresponding wet cells. The cells obtained above produced corresponding proteins, which can be used for preparing pure protein enzyme liquid, or can be used for catalysis in the form of crude enzyme liquid to obtain L-PPT. FIG. 3 is a corresponding protein GE image, wherein Lanes 1, 4, 7, 10 and 13 represents Marker; Lanes 2 and 3 represent the supernatant and precipitate of PhPPTDH-E263N; Lanes 5 and 6 represent the supernatant and precipitate of PhPPTDH-E263C; Lanes 8 and 9 represent the supernatant and precipitate of PhPPTDH-E263N; Lanes 11 and 12 represent the supernatant and precipitate of PhPPTDHE263G; and Lanes 14 and 15 represent the supernatant and precipitate of PhPPTDH.

Example 6

Screening of Phosphinothricin Dehydrogenase Mutant Library

The wet cells of mutant strains with induced expression were placed in a refrigerator at −20° C. to freeze overnight, re-suspended at an amount of 40 g/L total cells in a 100 mM phosphate buffer at pH 7.4, and allowed to melt on ice to obtain a crude enzyme liquid of the mutant strain. Under the same conditions, a crude enzyme liquid of the original strain was prepared using the original strain instead of the mutant strain. 200 mM glucose and 240 mM ammonium sulfate were dissolved in 10 mL of phosphate buffer (100 mM) at pH 8.5. 500 μL of the original solution was added to 500 μL of the crude enzyme solution of the different mutants from Example 2 (1 g of wet cells in 10 mL of a 100 mM phosphate buffer at pH 7.4), 1 mM NAD was added, the mixture was shaken at 35° C. and 600 rpm for 10 min, and then the reaction was terminated by adding 10 μL of 6 M HCl. The product concentration was detected by HPLC, and the dominant mutants were screened using the product L-phosphinothricin and e.e. value as indicators. The experimental results are shown in Table 2. Among others, E. coli BL21 (DE3)/PhPPTDH(E263D-K134R-H96A-R290V)-EsGDH was the most dominant strain, and the PHPPTDH gene of this dominant strain had a four-site mutation E263D-K134R-H96A-R290V.

Chiral analysis and concentration analysis of the products in the example were performed by pre-column derivatization high performance liquid chromatography, which specifically consisted of:

(1) Chromatographic conditions: column model: QS-C18, 5 μm, 4.6×250 mm; mobile phase: 50 mM ammonium acetate solution:methanol=10:1; fluorescence detection wavelength: $\lambda_{ex}$=340 nm, $\lambda_{em}$=455 nm; flow rate: 1 mL/min; column temperature: 30° C., L-PPT retention time: 11 min, and D-PPT retention time: 13.4 min.

(2) Derivatization reagent: 0.1 g of o-phthalaldehyde and 0.12 g of N-acetyl-L-cysteine were weighed separately and dissolved in 10 mL of ethanol, 40 mL of 0.1 mol/L boric acid buffer (pH 9.8) was added and the mixture was shaken to fully dissolve and then stored in a refrigerator at 4° C. for later use (no more than 4 days).

(3) Derivatization reaction and HPLC detection: Ultrapure water was used to make up to 1 mL, i.e., the reaction mixture was diluted 10 times. The diluted sample was subjected to derivatization treatment. To 200 μL of the diluted reaction mixture, 400 μL of the derivatization reagent was added for derivatization at 30° C. for 5 min, and then 400 μL of ultra-pure water was added to make up to 1 mL. The mixture was centrifuged at 12000 rpm for 1 min. The supernatant was passed through a 0.22 μM microfiltration membrane as a liquid sample, and detected for PPO, L-PPT, D-PPT, and e.e. value by HPLC.

TABLE 2

Catalytic performance and stereoselectivity of PhPPTDH and mutants thereof

| Corresponding PhPPTDH mutant for strain | Mutated bases and corresponding amino acids | Relative enzyme activity (%) | Enzyme activity (U/g) | e.e. value (%) |
|---|---|---|---|---|
| PhPPTDH | — | 100[a] | 32.75 | 99.5 |
| PhPPTDH(E263D) | GAA→GAT(E263D) | 600 | 196.7 | 99.5 |
| PhPPTDH(E263N) | GAA→TTA(E263N) | 371 | 121.65 | 99.5 |
| PhPPTDH(E263C) | GAA→ACA(E263C) | 463 | 151.55 | 99.5 |
| PhPPTDH(E263G) | GAA→CCT(E263G) | 484 | 158.45 | 99.5 |
| PhPPTDH(E263D-K134R) | GAA → GAT(E263D) AAG→CGA(K134R) | 492 | 165.7 | 99.5 |
| PhPPTDH(E263D-K134R-H96A) | GAA → GAT(E263D) AAG→CGA(K134R) CAC→GCA(H96A) | 609 | 205.2 | 99.5 |
| PhPPTDH(E263D-K134R-H96A-R290V) | GAA → GAT(E263D) AAG→CGA(K134R) CAC→GCA(H96A) CGC→GTA(R290V) | 666 | 224.5 | 99.5 |
| PhPPTDH | — | 100[b] | 137.3 | 99.5 |
| PhPPTDH(E263D) | GAA→GAT(E263D) | 224 | 307.2 | 99.5 |
| PhPPTDH(E263N) | GAA→TTA(E263N) | 220 | 305.4 | 99.5 |
| PhPPTDH(E263C) | GAA→ACA(E263C) | 209 | 287.2 | 99.5 |
| PhPPTDH(E263G) | GAA→CCT(E263G) | 224 | 306.5 | 99.5 |
| PhPPTDH(E263D-K134R) | GAA → GAT(E263D) AAG-CGA(K134R) | 208 | 285.8 | 99.5 |
| PhPPTDH(E263D-K134R-H96A) | GAA → GAT(E263D) AAG→CGA(K134R) CAC→GCA(H96A) | 215 | 295.3 | 99.5 |
| PhPPTDH(E263D-K134R-H96A-R290V) | GAA → GAT(E263D) AAG→CGA(K134R) CAC→GCA(H96A) CGC→GTA(R290V) | 319 | 437.6 | 99.5 |

[a]Under the standard conditions, with NAD as the coenzyme, the enzyme activity of PhPPTDH was 100%.
[b]Under the standard conditions, with NADP as the coenzyme, the enzyme activity of PhPPTDH was 100%.

Example 7

Figure 4:
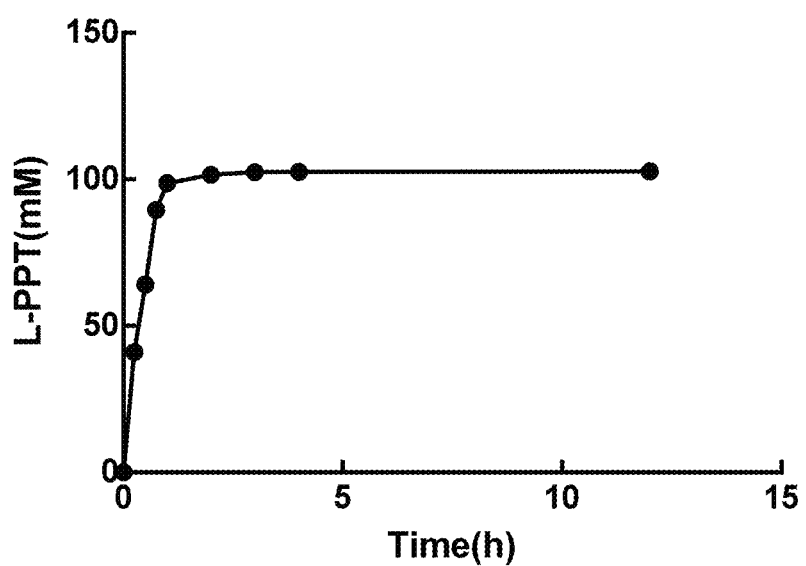
FIG. 4 is a reaction process diagram showing preparation of 100 ml of L-PPT by asymmetric reductive amination using the phosphinothricin dehydrogenase mutant PhPPTDH-E263D-K134R-H96A-R290V in Example 7.

Asymmetric Reductive Amination of Low Concentration of 2-carbonyl-4-(hydroxymethylphosphinyl)-butyric Acid (PPO) Using Phosphinothricin Dehydrogenase Mutant Coupled with Glucose Dehydrogenase 1 g of E. coli BL21 (DE3)/PhPPTDH(E263D-K134R-H96A-R290V)-EsGDH wet cells prepare by the method of Example 6 were re-suspended with 50 mL of phosphate buffer (100 mM) at pH 7.4, and 2-carbonyl-4-(hydroxymethylphosphinyl)-butyric acid with a final concentration of 100 mM, glucose with a final concentration of 110 mM, and ammonium sulfate with a final concentration of 120 mM were added to form a reaction system of 50 mL to react at 35° C. and a magnetic stirring speed of 600 rpm, and ammonia was fed to maintain the pH of the reaction mixture at 7.4. The production of the product L-phosphinothricin during the reaction was detected by the liquid phase method shown in Example 4, and the reaction progress curve is shown in FIG. 4. It is shown that the product concentration gradually increased with the passage of time, and the reaction was completed within 1 hour, with the substrate conversion greater than 99%, indicating that the mutant PhPPTDH-E263D-K134R-H96A-R290V had high efficiency in asymmetrically catalyzing the amino translocation reaction of 2-carbonyl-4-(hydroxymethylphosphonyl)-butyric acid.

Example 8

Figure 5:
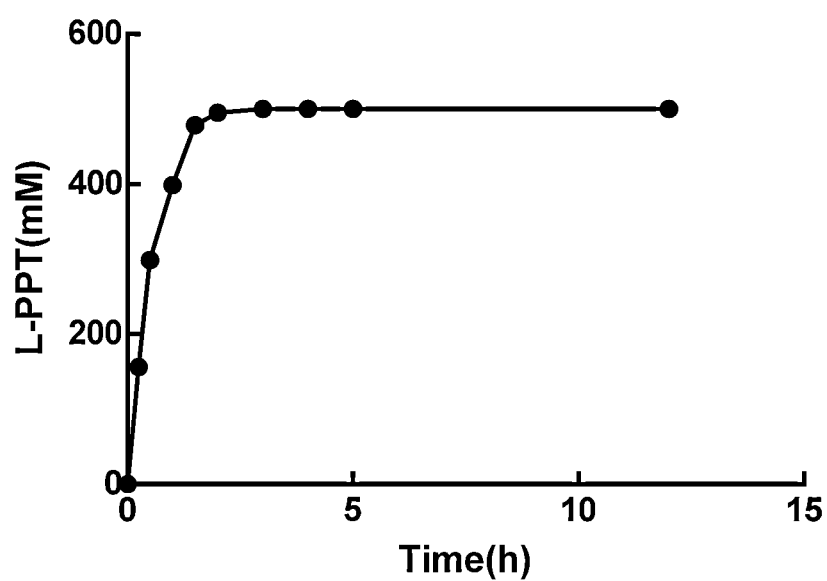
FIG. 5 is a reaction process diagram showing preparation of 500 ml of L-PPT by asymmetric reductive amination using the phosphinothricin dehydrogenase mutant PhPPTDH-E263D-K134R-H96A-R290V in Example 8.

Asymmetric Reductive Amination of High Concentration of 2-carbonyl-4-(hydroxymethylphosphinyl)-butyric Acid (PPO) Using Phosphinothricin Dehydrogenase Mutant Coupled with Glucose Dehydrogenase 1 g of E. coli BL21 (DE3)/PhPPTDH(E263D-K134R-H96A-R290V)-EsGDH wet cells prepare by the method of Example 6 were re-suspended with 100 mL of phosphate buffer (100 mM) at pH 7.4, and 2-carbonyl-4-(hydroxymethylphosphinyl)-butyric acid with a final concentration of 500 mM, glucose with a final concentration of 510 mM, and ammonium sulfate with a final concentration of 520 mM were added to form a reaction system of 50 mL to react at 35° C. and a magnetic stirring speed of 600 rpm, and ammonia was fed to maintain the pH of the reaction mixture at 7.4. The production of the product L-phosphinothricin during the reaction was detected by the liquid phase method shown in Example 4, and the reaction progress curve is shown in FIG. 5. It is shown that the product concentration gradually increased with the passage of time, and the reaction was completed within 2 h, with the substrate conversion greater than 99%, indicating that the mutant PhPPTDH-E263D-K134R-H96A-R290V had high efficiency in asymmetrically catalyzing the amino translocation reaction of high concentration of 2-carbonyl-4-(hydroxymethylphosphonyl)-butyric acid.

Comparative Example 1

Asymmetric Reductive Amination of Low Concentration of 2-carbonyl-4-(hydroxymethylphosphinyl)-butyric Acid (PPO) Using Wild-Type Phosphinothricin Dehydrogenase Coupled with Glucose Dehydrogenase 1 g of E. coli BL21 (DE3)/PhPPTDH-EsGDH wet cells prepare by the method of Example 2 were re-suspended with 50 mL of phosphate buffer (100 mM) at pH 7.4, and 2-carbonyl-4-(hydroxymethylphosphinyl)-butyric acid with a final concentration of 100 mM, glucose with a final concentration of 110 mM, and ammonium sulfate with a final concentration of 120 mM were added. The reaction system was 50 mL, the temperature was 35° C., and the magnetic stirring speed was 600 rpm. The production of the product L-phosphinothricin during the reaction was detected by the liquid phase method shown in Example 4. After 4 hours of reaction, the substrate conversion was only 64%.

Comparative Example 2

Asymmetric Reductive Amination of High Concentration of 2-carbonyl-4-(hydroxymethylphosphinyl)-Butyric Acid (PPO) Using Wild-Type Phosphinothricin Dehydrogenase Coupled with Glucose Dehydrogenase 1 g of E. coli BL21 (DE3)/PhPPTDH-EsGDH wet cells prepare by the method of Example 2 were re-suspended with 100 mL of phosphate buffer (100 mM) at pH 7.4, and 2-carbonyl-4-(hydroxymethylphosphinyl)-butyric acid with a final concentration of 500 mM, glucose with a final concentration of 510 mM, and ammonium sulfate with a final concentration of 520 mM were added. The reaction system was 50 mL, the temperature was 35° C., and the magnetic stirring speed was 600 rpm. Ammonia was fed to maintain the pH of the reaction mixture at 7.4. The production of the product L-phosphinothricin during the reaction was detected by the liquid phase method shown in Example 4. After 4 hours of reaction, the substrate conversion was only 35%.

What is claimed is:

1. A phosphinothricin dehydrogenase mutant for amino translocation with the amino acid sequence of wild-type phosphinothricin dehydrogenase from *Pseudomonas hunanensis* as shown in SEQ ID NO: 2 except having one of the following sites of mutation:
(1) E263D-K134R-H96A-R290V;
(2) E263D-K134R-H96A;
(3) E263D-K134R;
(4) E263D;
(5) E263N;
(6) E263C; or
(7) E263G.

2. A gene encoding the phosphinothricin dehydrogenase mutant for amino translocation according to claim 1.

3. A genetically recombinant bacterium comprising a host cell and a target gene transformed into the host cell, wherein the target gene comprises the gene according to claim 2.

4. The genetically recombinant bacterium according to claim 3, wherein the genetically recombinant bacterium further comprises a gene encoding a glucose dehydrogenase transformed into the host cell.

5. The phosphinothricin dehydrogenase mutant for amino translocation according to claim 1, wherein the site of mutation is: E263D-K134R-H96A-R290V.

6. A method for preparing L-phosphinothricin, by reacting 2-carbonyl-4-(hydroxymethylphosphono)butyric acid as a substrate as catalyzed by a catalyst in the presence of an inorganic amino donor, a coenzyme circulation system and a corresponding co-substrate of the coenzyme circulation system to obtain L-phosphinothricin; wherein
the catalyst is one of:
(1) the phosphinothricin dehydrogenase mutant for amino translocation according to claim 1; and
(2) a genetically recombinant bacterium producing the phosphinothricin dehydrogenase mutant for amino translocation according to claim 1, or a crude enzyme liquid containing the phosphinothricin dehydrogenase mutant obtained by lysis of the genetically recombinant bacterium.

7. The method according to claim 6, wherein the coenzyme circulation system is at least one of:

(1) a formate dehydrogenase coenzyme circulation system comprising a formate dehydrogenase, formate and a coenzyme;
(2) a glucose dehydrogenase coenzyme circulation system comprising a glucose dehydrogenase, glucose and a coenzyme; and
(3) an alcohol dehydrogenase coenzyme circulation system comprising an alcohol dehydrogenase, isopropanol and a coenzyme.

8. The method according to claim 7, wherein the coenzyme circulation system is a formate dehydrogenase coenzyme circulation system comprising a formate dehydrogenase, formate and a coenzyme.

* * * * *

SEQUENCE LISTING

```
<160> NUMBER OF SEQ ID NOS: 23

<210> SEQ ID NO 1
<211> LENGTH: 1341
<212> TYPE: DNA
<213> ORGANISM: Pseudomonas hunanensis

<400> SEQUENCE: 1
atgatcgaat ctgtcgacaa tttccttgca cgcctgcaac agcgtgaccc tggccaaccg      60
gaattccacc aggcggtgga agaggtgttg cgcaccctgt ggccattcct tgaagccaac     120
cctcactacc tgcaatccgg catcctcgag cgcatggtcg agcccgagcg cgctgtactg     180
tttcgcgtgt cctgggtcga tgaccagggc aaggtgcagg tcaatcgcgg ttaccgcatc     240
cagatgagca gcgccattgg cccgtacaag ggcgggctgc gtttccaccc gtcggttaac     300
ctcagcgtgc tgaagttcct ggccttcgag caagtgttca agaactccct gacctcgctg     360
cccatgggcg gcggcaaggg cggctcggac ttcgacccta aaggcaagag cgacgctgaa     420
gtgatgcgct tctgccaggc cttcatgagc gagctgtacc gccacatcgg cgccgactgc     480
gacgtaccgg ccggtgacat cggtgtgggc gcccgcgaaa tcggcttcat gttcggccag     540
tacaaacgcc tggccaacca gttcacctcg gtgttgaccg gcaaaggcat gacctacggc     600
```

```
ggcagcctga tccgtccgga agccaccggc tatggctgcg tgtacttcgc cgaagaaatg    660
ctcaaacgcc aggacaagcg tatcgacggt cgccgcgtgg cggtgtccgg ttcgggcaac    720
gttgcccagt atgccacgcg caaggtcatg gacctgggcg gcaaggtgat ttcgctgtct    780
gactccgaag gcaccttgta cgctgaagcc ggcttgaccg atgcccagtg ggacgccttg    840
atggagctga gaacgtcaa gcgcggccgc atcagcgagc tggccgggca gttcggcctg    900
gagttccgca aggccagac cccatggagc ctgccgtgcg acatcgccct gccgtgcgcc    960
acgcagaacg aactgggcgc cgaggacgcc cgcacgctgc tgcgtaacgg ctgcatctgc   1020
gtggctgaag cgccaacat gccgaccacc ctggaagctg tggatatctt cctggacgcc   1080
ggcatcctgt acgccccggg caaggcctcc aacgccggtg gcgtggccgt atcgggcctg   1140
gaaatgtcgc agaacgccat gcgcctgctg tggactgccg tgaagtgga cagcaagctg   1200 cacaacatca tgcagtcgat tcaccatgca tgcgtgcact acggtgaaga agccgatggc   1260
cgtatcaact acgtcaaagg tgcgaacatc gcaggctttg tgaaagtggc cgatgcgatg   1320
ctggctcagg gcgtcgtctg a                                             1341

<210> SEQ ID NO 2
<211> LENGTH: 446
<212> TYPE: PRT
<213> ORGANISM: Pseudomonas hunanensis

<400> SEQUENCE: 2

Met Ile Glu Ser Val Asp Asn Phe Leu Ala Arg Leu Gln Gln Arg Asp
1               5                   10                  15

Pro Gly Gln Pro Glu Phe His Gln Ala Val Glu Val Leu Arg Thr
            20                  25                  30

Leu Trp Pro Phe Leu Glu Ala Asn Pro His Tyr Leu Gln Ser Gly Ile
        35                  40                  45

Leu Glu Arg Met Val Glu Pro Glu Arg Ala Val Leu Phe Arg Val Ser
    50                  55                  60

Trp Val Asp Asp Gln Gly Lys Val Gln Val Asn Arg Gly Tyr Arg Ile
65                  70                  75                  80

Gln Met Ser Ser Ala Ile Gly Pro Tyr Lys Gly Gly Leu Arg Phe His
                85                  90                  95

Pro Ser Val Asn Leu Ser Val Leu Lys Phe Leu Ala Phe Glu Gln Val
            100                 105                 110

Phe Lys Asn Ser Leu Thr Ser Leu Pro Met Gly Gly Gly Lys Gly Gly
        115                 120                 125

Ser Asp Phe Asp Pro Lys Gly Lys Ser Asp Ala Glu Val Met Arg Phe
    130                 135                 140

Cys Gln Ala Phe Met Ser Glu Leu Tyr Arg His Ile Gly Ala Asp Cys
145                 150                 155                 160

Asp Val Pro Ala Gly Asp Ile Gly Val Gly Ala Arg Glu Ile Gly Phe
                165                 170                 175

Met Phe Gly Gln Tyr Lys Arg Leu Ala Asn Gln Phe Thr Ser Val Leu
            180                 185                 190

Thr Gly Lys Gly Met Thr Tyr Gly Gly Ser Leu Ile Arg Pro Glu Ala
        195                 200                 205

Thr Gly Tyr Gly Cys Val Tyr Phe Ala Glu Glu Met Leu Lys Arg Gln
    210                 215                 220

Asp Lys Arg Ile Asp Gly Arg Arg Val Ala Val Ser Gly Ser Gly Asn
225                 230                 235                 240
```

```
Val Ala Gln Tyr Ala Thr Arg Lys Val Met Asp Leu Gly Gly Lys Val
                245                 250                 255

Ile Ser Leu Ser Asp Ser Glu Gly Thr Leu Tyr Ala Glu Ala Gly Leu
            260                 265                 270

Thr Asp Ala Gln Trp Asp Ala Leu Met Glu Leu Lys Asn Val Lys Arg
        275                 280                 285

Gly Arg Ile Ser Glu Leu Ala Gly Gln Phe Gly Leu Glu Phe Arg Lys
    290                 295                 300

Gly Gln Thr Pro Trp Ser Leu Pro Cys Asp Ile Ala Leu Pro Cys Ala
305                 310                 315                 320

Thr Gln Asn Glu Leu Gly Ala Glu Asp Ala Arg Thr Leu Leu Arg Asn
                325                 330                 335

Gly Cys Ile Cys Val Ala Glu Gly Ala Asn Met Pro Thr Thr Leu Glu
            340                 345                 350

Ala Val Asp Ile Phe Leu Asp Ala Gly Ile Leu Tyr Ala Pro Gly Lys
        355                 360                 365

Ala Ser Asn Ala Gly Gly Val Ala Val Ser Gly Leu Glu Met Ser Gln
    370                 375                 380

Asn Ala Met Arg Leu Leu Trp Thr Ala Gly Glu Val Asp Ser Lys Leu
385                 390                 395                 400

His Asn Ile Met Gln Ser Ile His His Ala Cys Val His Tyr Gly Glu
                405                 410                 415

Glu Ala Asp Gly Arg Ile Asn Tyr Val Lys Gly Ala Asn Ile Ala Gly
            420                 425                 430

Phe Val Lys Val Ala Asp Ala Met Leu Ala Gln Gly Val Val
        435                 440                 445

<210> SEQ ID NO 3
<211> LENGTH: 6
<212> TYPE: PRT
<213> ORGANISM: Artificial Sequence
<220> FEATURE:
<223> OTHER INFORMATION: Synthesized

<400> SEQUENCE: 3

Gly Gly Gly Lys Gly Gly
1               5

<210> SEQ ID NO 4
<211> LENGTH: 4
<212> TYPE: PRT
<213> ORGANISM: Artificial Sequence
<220> FEATURE:
<223> OTHER INFORMATION: Synthesized

<400> SEQUENCE: 4

Val Val Thr Gly
1

<210> SEQ ID NO 5
<211> LENGTH: 4
<212> TYPE: PRT
<213> ORGANISM: Artificial Sequence
<220> FEATURE:
<223> OTHER INFORMATION: Synthesized

<400> SEQUENCE: 5

Phe Val Thr Gly
1
```

```
<210> SEQ ID NO 6
<211> LENGTH: 4
<212> TYPE: PRT
<213> ORGANISM: Artificial Sequence
<220> FEATURE:
<223> OTHER INFORMATION: Synthesized

<400> SEQUENCE: 6

Val Leu Thr Gly
1

<210> SEQ ID NO 7
<211> LENGTH: 4
<212> TYPE: PRT
<213> ORGANISM: Artificial Sequence
<220> FEATURE:
<223> OTHER INFORMATION: Synthesized

<400> SEQUENCE: 7

Val Leu Thr Gly
1

<210> SEQ ID NO 8
<211> LENGTH: 4
<212> TYPE: PRT
<213> ORGANISM: Artificial Sequence
<220> FEATURE:
<223> OTHER INFORMATION: Synthesized

<400> SEQUENCE: 8

Phe Ile Thr Gly
1

<210> SEQ ID NO 9
<211> LENGTH: 4
<212> TYPE: PRT
<213> ORGANISM: Artificial Sequence
<220> FEATURE:
<223> OTHER INFORMATION: Synthesized

<400> SEQUENCE: 9

Phe Phe Thr Gly
1

<210> SEQ ID NO 10
<211> LENGTH: 4
<212> TYPE: PRT
<213> ORGANISM: Artificial Sequence
<220> FEATURE:
<223> OTHER INFORMATION: Synthesized

<400> SEQUENCE: 10

Val Val Phe Gly
1

<210> SEQ ID NO 11
<211> LENGTH: 5
<212> TYPE: PRT
<213> ORGANISM: Artificial Sequence
<220> FEATURE:
<223> OTHER INFORMATION: Synthesized

<400> SEQUENCE: 11

Phe Val Phe Thr Gly
1               5
```

```
<210> SEQ ID NO 12
<211> LENGTH: 4
<212> TYPE: PRT
<213> ORGANISM: Artificial Sequence
<220> FEATURE:
<223> OTHER INFORMATION: Synthesized

<400> SEQUENCE: 12

Val Leu Phe Gly
1

<210> SEQ ID NO 13
<211> LENGTH: 4
<212> TYPE: PRT
<213> ORGANISM: Artificial Sequence
<220> FEATURE:
<223> OTHER INFORMATION: Synthesized

<400> SEQUENCE: 13

Val Phe Phe Gly
1

<210> SEQ ID NO 14
<211> LENGTH: 4
<212> TYPE: PRT
<213> ORGANISM: Artificial Sequence
<220> FEATURE:
<223> OTHER INFORMATION: Synthesized

<400> SEQUENCE: 14

Phe Leu Phe Gly
1

<210> SEQ ID NO 15
<211> LENGTH: 4
<212> TYPE: PRT
<213> ORGANISM: Artificial Sequence
<220> FEATURE:
<223> OTHER INFORMATION: Synthesized

<400> SEQUENCE: 15

Phe Phe Phe Gly
1

<210> SEQ ID NO 16
<211> LENGTH: 29
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (11)..(12)
<223> OTHER INFORMATION: n stands for a, c, g or t
<220> FEATURE:
<221> NAME/KEY: misc_feature
<222> LOCATION: (13)..(13)
<223> OTHER INFORMATION: k stands for g or t

<400> SEQUENCE: 16
gtctgactcc nnkggcacct tgtacgctg                                    29

<210> SEQ ID NO 17
<211> LENGTH: 29
<212> TYPE: DNA
<213> ORGANISM: Artificial Sequence
<220> FEATURE:
<223> OTHER INFORMATION: Synthesized
<220> FEATURE:
```

```
<221> NAME/KEY: misc_feature
<222> LOCATION: (12)..(12)
<223> OTHER INFORMATION: m stands for a or c.
<220> FEATURE:
<221> NAME/KEY: misc_feature
<222> LOCATION: (13)..(14)
<223> OTHER INFORMATION: n stands for a, c, g or t.

<400> SEQUENCE: 17
tacaaggtgc cmnnggagtc agacagcga                                29

<210> SEQ ID NO 18
<211> LENGTH: 29
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (8)..(9)
<223> OTHER INFORMATION: n stands for a, c, g or t.
<220> FEATURE:
<221> NAME/KEY: misc_feature
<222> LOCATION: (10)..(10)
<223> OTHER INFORMATION: k stands for g or t.

<400> SEQUENCE: 18
cgaccctnnk ggcaagagcg acgctgaag                                29

<210> SEQ ID NO 19
<211> LENGTH: 29
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (13)..(13)
<223> OTHER INFORMATION: m stands for a or c.
<220> FEATURE:
<221> NAME/KEY: misc_feature
<222> LOCATION: (14)..(15)
<223> OTHER INFORMATION: n stands for a, c, g or t.

<400> SEQUENCE: 19
gtcgctcttg ccmnnagggt cgaagtccg                                29

<210> SEQ ID NO 20
<211> LENGTH: 29
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (9)..(10)
<223> OTHER INFORMATION: n stands for a, c, g or t.
<220> FEATURE:
<221> NAME/KEY: misc_feature
<222> LOCATION: (11)..(11)
<223> OTHER INFORMATION: k stands for g or t.

<400> SEQUENCE: 20
tgcgtttcnn kccgtcggtt aacctcagc                                29

<210> SEQ ID NO 21
<211> LENGTH: 29
<212> TYPE: DNA
<213> ORGANISM: Artificial Sequence
<220> FEATURE:
<223> OTHER INFORMATION: Synthesized
```

```
<220> FEATURE:
<221> NAME/KEY: misc_feature
<222> LOCATION: (9)..(9)
<223> OTHER INFORMATION: m stands for a or c.
<220> FEATURE:
<221> NAME/KEY: misc_feature
<222> LOCATION: (10)..(11)
<223> OTHER INFORMATION: n stands for a, c, g or t.

<400> SEQUENCE: 21
accgacggmn ngaaacgcag cccgccctt                                29

<210> SEQ ID NO 22
<211> LENGTH: 29
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (8)..(9)
<223> OTHER INFORMATION: n stands for a, c, g or t.
<220> FEATURE:
<221> NAME/KEY: misc_feature
<222> LOCATION: (10)..(10)
<223> OTHER INFORMATION: k stands for g or t.

<400> SEQUENCE: 22
gcgcggcnnk atcagcgagc tggccgggc                                29

<210> SEQ ID NO 23
<211> LENGTH: 29
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (15)..(15)
<223> OTHER INFORMATION: m stands for a or c.
<220> FEATURE:
<221> NAME/KEY: misc_feature
<222> LOCATION: (16)..(17)
<223> OTHER INFORMATION: n stands for a, c, g or t.

<400> SEQUENCE: 23
tcgctgatgc ggccmnnctt gacgttctt                                29
```